(12) United States Patent
Huppé et al.

(10) Patent No.: US 6,713,460 B2
(45) Date of Patent: Mar. 30, 2004

(54) GLASS-LIKE POLYSACCHARIDE USEFUL AS ABSORBENT FOR LIQUIDS

(75) Inventors: Serge Huppé, Québec (CA); Marie-Elise Maheux, Québec (CA); Stéphane Chevigny, Québec (CA); Francois Quirion, Québec (CA)

(73) Assignee: Groupe Lysac Inc., Quebec (CA)

( * ) Notice: Subject to any disclaimer, the term of this patent is extended or adjusted under 35 U.S.C. 154(b) by 0 days.

(21) Appl. No.: 10/115,412

(22) Filed: Apr. 3, 2002

(65) Prior Publication Data

US 2002/0156048 A1 Oct. 24, 2002

Related U.S. Application Data

(63) Continuation of application No. 09/569,275, filed on May 11, 2000, now Pat. No. 6,444,653.

(30) Foreign Application Priority Data

May 11, 1999 (CA) ............................................. 2271425

(51) Int. Cl.⁷ .......................... A61K 31/70; A61F 13/15
(52) U.S. Cl. ........................ 514/54; 536/123.1; 604/367
(58) Field of Search ........................... 514/54; 604/367; 536/123.1

(56) References Cited

U.S. PATENT DOCUMENTS

| | | | |
|---|---|---|---|
| 3,706,598 A | 12/1972 | Carrell ........................ 127/29 |
| 4,935,022 A | 6/1990 | Lash et al. ................... 604/375 |
| 5,026,363 A | 6/1991 | Pratt ........................ 604/385.1 |
| 5,047,023 A | 9/1991 | Berg ........................... 604/368 |
| 5,061,259 A | 10/1991 | Goldman et al. ........... 604/368 |
| 5,360,903 A | 11/1994 | Lane et al. .................. 536/124 |
| 5,743,895 A | 4/1998 | Reiss et al. ................. 604/377 |
| 6,015,608 A | 1/2000 | Koslow ................... 428/304.4 |

OTHER PUBLICATIONS

Buchholz, Frederic L., Graham, Andrew T.; Modern Superabsorbent Polymer Technology, pp. 103, 265–266, 269–272, Wiley–VCH.

*Primary Examiner*—Elli Peselev
(74) *Attorney, Agent, or Firm*—Bourque & Associates, P.A.

(57) ABSTRACT

A particulate absorbent, for the absorption of liquids, comprising particles selected from the group consisting of particles of glass-like polysaccharides and of particles of glass-like polysaccharides occluding, in their internal structure, at least one surfactant, said particles:

having a size of up to 620 μm;
being at least 70% of a glass-like type structure; and
being:
  30 to 45% of a size comprised between 620 and 420 μm;
  35 to 55% of a size comprised between 420 and 210 μm; and
  5 to 25% of a size up to 210 μm.

These particulate absorbent is non-hygroscopic, hypoallergenic and biodegradable and useful particularly in biodegradable diapers.

12 Claims, 5 Drawing Sheets

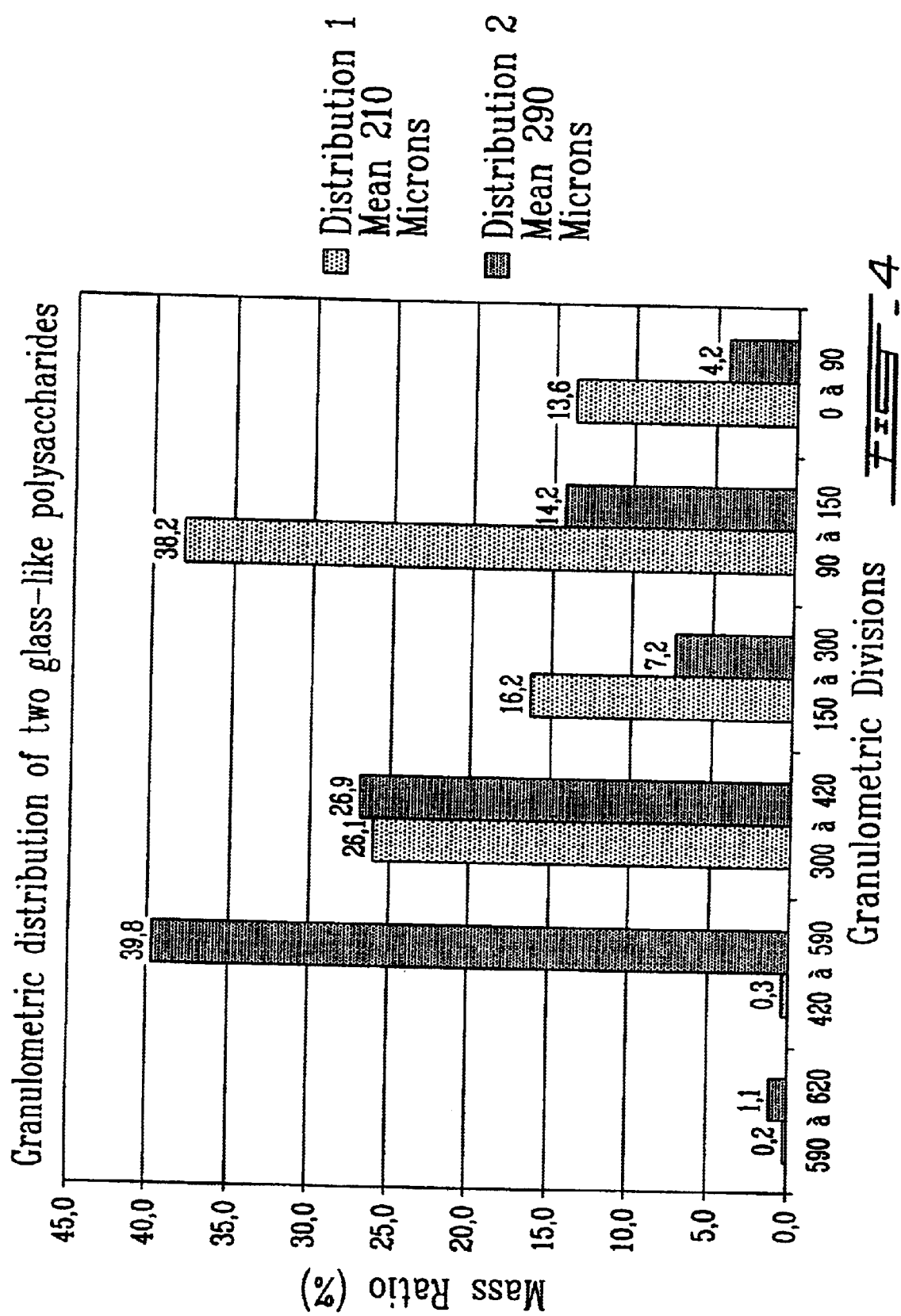

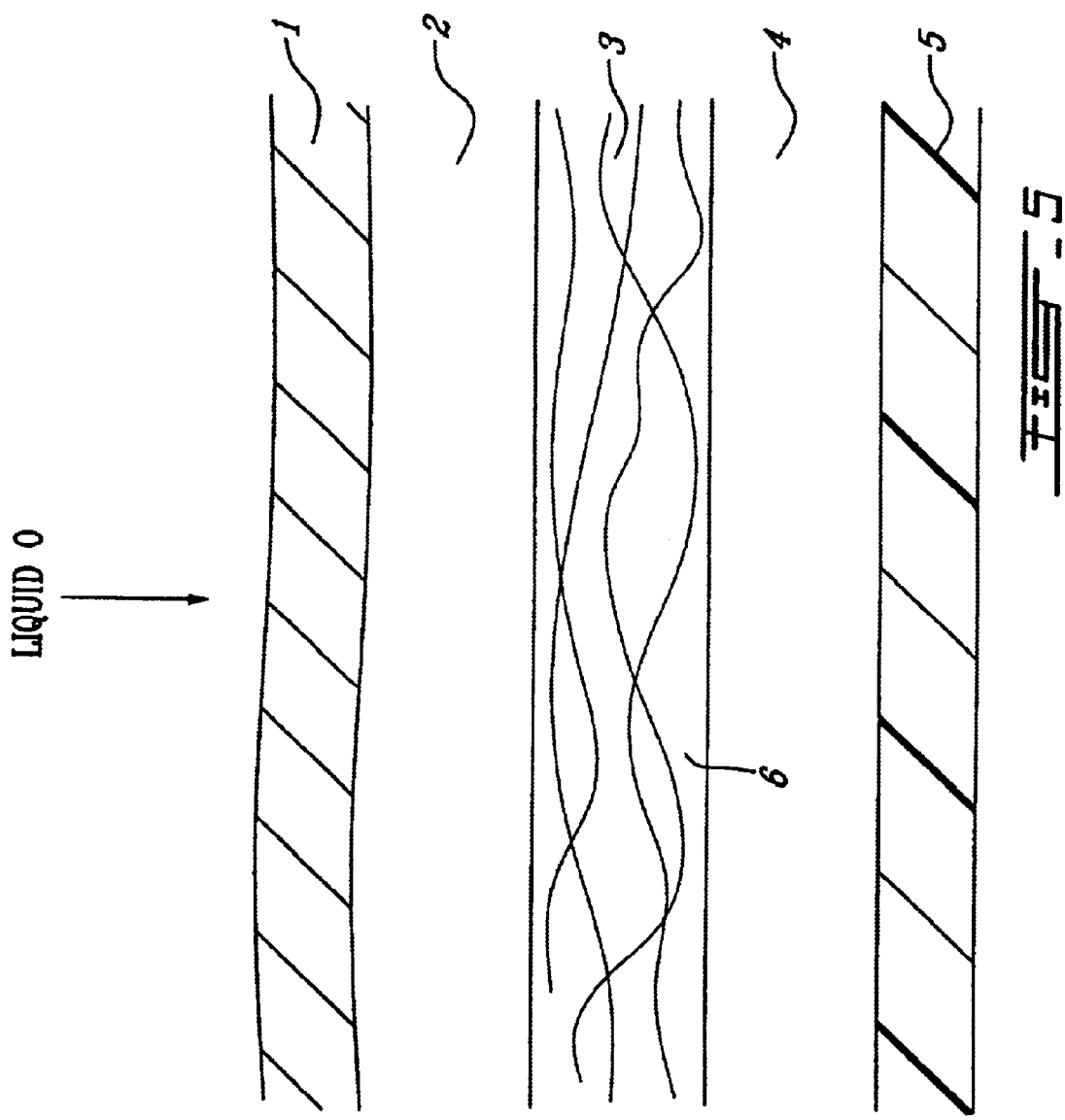

GLASS-LIKE POLYSACCHARIDE USEFUL AS ABSORBENT FOR LIQUIDS

CROSS-REFERENCE TO RELATED APPLICATIONS

The present application is a continuation of U.S. patent application Ser. No. 09/569,275 filed May 11, 2000, now U.S. Pat. No. 6,444,653 B1.

FIELD OF THE INVENTION

The present invention relates to a particulate absorbent, for the absorption of liquids, comprising particles selected from the group consisting of particles of glass-like polysaccharides and of particles of glass-like polysaccharides occluding, in their internal structure, at least one surfactant.

The present invention further relates to the use of the latter particulate absorbent alone or in combination with additives or intrants, as absorbent of polar liquids and of physiological fluids and more particularly relates to specific absorbent compositions of the particulate absorbent according to the invention with selected carboxymethylcelluloses and/or with selected gums.

The present invention also concerns absorbent combinations of a predetermined amount of at least one particulate absorbent and/or of a predetermined amount of at least one absorbent composition with a suitable carrier.

BACKGROUND

Various glass-like polysaccharides are known in the art. For example U.S. Pat. No. 5,360,903 describes glass-like polysaccharides and glass-like starches having a substantially occluded water component. Such polysaccharides are useful for abrading surfaces.

Diapers and more particularly sanitary napkins are traditionally constituted by a first external layer permeable to physiological fluids, a central matrix essentially made of an absorbing material such as cloth, cotton, paper wadding or batts of cellulose fibre and a second external layer impermeable to physiological fluids and to aggregates formed by the physiological fluids with the absorbing material present in the central matrix. The central matrix is entrapped between both layers. The central matrix of diapers, originally essentially made of pads of fluffed cellulose pulp fibres, have over a time span of about 20 years gradually been substituted by synthetic absorbent polymers and by synthetic superabsorbent polymers in the form of a hard, dry, granular powder. A detailed description of such absorbent is given in Modern Superabsorbent Polymer Technology, by Frederic L. Buchholz and A. T. Graham, edited by Wiley-VCH, pages 1 to 16 which document is thereby incorporated by reference.

Pads of fluffed cellulose pulp fibres absorb about 12 grams of water whereas a superabsorbent polymer may absorb up to one thousand (1,000) grams of water per gram of polymer.

However such a high performance is only reached with solutions in distilled aqueous water. Such superabsorbents lose rapidly their performances in solutions with a high ionic content.

However superabsorbent polymers are not used alone, but typically used in admixture with at least one another material with absorbing properties, in order to improve the absorbing profile. For example, superabsorbent polymer granules are mixed with wood pulp fluff in diapers.

Those superabsorbent polymers mainly used commercially are cross linked, partially neutralized poly(acrylic acid) or graft copolymers such as partially neutralized starch-g-poly(acrylic acid) and partially neutralized poly(vinyl alcohol)-g-poly(acrylic acid). Others well-known superabsorbent polymers are hydrolysed starches-g-poly(acrylonitrile).

Intensive searches have been performed in order to improve the absorbency of known synthetic and semi-synthetic superabsorbents. Thus U.S. Pat. No. 4,935,022 describes absorbent articles which utilize a particular type of stiffened cellulose fibers and a particular type and form of polymeric gelling agent particles to enhance the absorbency characteristics of such articles. In these articles, the gelling agent material, combined in particulate form of a certain size with stiffened cellulose fiber material, is primarily placed in a lower fluid storage layer of the absorbent core of the article. Such a fluid storage lower layer of the absorbent core is placed underneath an upper, generally larger, fluid acquisition/distribution layer which also contains stiffened cellulose fibers and gelling agent particles of a certain size. The gelling particles have a mass median particle size ranging from about 400 to 1680 microns. The mentioned gelling agent is a substantially water-insoluble slightly, partially neutralized polymer selected from hydrolysed acrylonitrile grafted starch, polyacrylates, maleic anhydride-based copolymers and combinations of these polymers therefore.

U.S. Pat. No. 5,047,023 describes an absorbent article wherein the deposition region of its absorbent member comprises a storage zone and a acquisition zone having a lower average density and a lower average basis weight per unit area than the storage area. The acquisition zone is positioned toward the front of either the absorbent member or the absorbent article so that the acquisition zone may most effectively and efficiently rapidly acquire discharged liquids.

The absorbent member comprises a mixture of a hydrophylic fibrous material and discrete particles of absorbent gelling material having a particle size distribution so as to enhance the absorbent capacity and acquisition rate of the absorbent member. The particles of the absorbent gelling material are selected to have a mass median particle size greater than or equal to about 400 microns with the amounts of very large and very small particles preferably kept below certain minimum concentrations. As suited absorbent gelling material particles are those already mentioned in U.S. Pat. No. 4,935,022. Mentioned as preferred absorbent gelling material are hydrolysed acrylonitrile grafted starches, acrylic acid grafted starches, polyacrylates, maleic anhydride copolymers and combination thereof.

U.S. Pat. No. 5,061,259 describes absorbent structures and absorbent gelling agent compositions suitable for use in disposable absorbent articles. The absorbent structures comprise hydrophylic fiber material and nonfragile particles of polymeric gelling agent. The gelling agent particles incorporated into such structures are selected to have a mass median particle size ranging from about 400 to 700 microns, with no more than about 16% by weight of said particles having a particle size less than 200 microns and no more than about 16% by weight of said particles having a particle size greater than 1000 microns. The gelling agent particles are preferably nonfragile particles of hydrogel-forming polymeric gelling agent with a specific granulometry and comprise a specific amount of the grafted starches already mentioned in U.S. Pat. No. 5,047,023 and in U.S. Pat. No. 4,935,022.

In spite of their advantages, the above mentioned synthetic or semi-synthetic superabsorbents, also called "super slurper", exhibit major drawbacks.

Most of the synthetic superabsorbents are not biodegradable and semi-synthetic superabsorbents are generally only slightly biodegradable.

Moreover, due to their hardness and to their chemical nature, particulates of synthetic superabsorbents and particulates of semi-synthetic superabsorbents generate irritability of intimate body parts.

Allergic reactions to synthetic or semi-synthetic superabsorbents, occurring inter alia when granulates of synthetic superabsorbents come in contact with mucous membranes, are commonly reported.

Furthermore, semi-synthetic and synthetic superabsorbents are hygroscopic. This tendency to absorb moisture represents a major drawback. Particularly for applications wherein a long retention time of the absorbed fluid is required.

Finally and in having regard to new environmental regulations, there is an increasing need for biodegradable hygiene products like diapers. Such a need resulted over the past years in intensive searches for new biodegradable hypoallergenic and non-hygroscopic polymeric materials with a high absorbency and with good stability in a wide pH range.

SUMMARY

A first object of the present invention is a particulate absorbent, for the absorption of liquids, comprising particles of glass-like polysaccharides and/or of particles of glass-like polysaccharides occluding, in their internal structure, at least one surfactant. The glass-like polysaccharides are characterized in that their particles have a specific granulometry. These particulate absorbent is biodegradable, non-hygroscopic, hypoallergenic and stable on a wide pH range.

A second object of the present invention is a process for preparing those particulates absorbent according to the first object of the invention wherein the glass-like polysaccharides occlude at least one surfactant, in their internal structure.

A third object of the present invention is an absorbing, particularly a biodegradable, non-hygroscopic and hypoallergenic absorbing composition comprising, in specific ranges, a particulate absorbent according to the first object of the invention, an insoluble carboxymethylcellulose and a high viscosity carboxymethylcellulose.

A fourth object of the present invention is an absorbing, particularly a biodegradable, hypoallergen and non-hygroscopic absorbing, composition comprising, in specific ranges: a particulate absorbent according to the first object of the invention, a xanthane gum and a guar gum.

A fifth object of the present invention is an absorbent combination of at least one particulate absorbent according to the first object of the invention and/or a absorbent composition according to the third or to the fourth object of the present invention with a suitable carrier.

A sixth object of the present invention is constituted by:

breast pads (nursing pads), food pads, diapers (disposable and non disposable infant diapers, training pants), adult incontinence products (personal pads, bed pads, briefs), feminine hygiene products (tampons, sanitary napkins), and surgery and surgical pads or bandages, in which a particulate absorbent according to the first object and/or an absorbing composition according to the third and/or to the fourth object of the present invention has been incorporated.

In general, in accordance with the present invention, there is provided a particulate absorbent, for the absorption of liquids, comprising particles of glass-like polysaccharides wherein said particles have a size of up to 620 µm. In general, in accordance with the present invention, there is also provided a particulate absorbent, for the absorption of liquids, comprising particles of glass-like polysaccharides occluding, in their internal structure, at least one surfactant wherein said particles have a size of up to 620 µm. In accordance with the present invention, the particles may be at least 70% by weight of a glass-like type structure. In accordance with the present invention, the particles may have a size in the range of from 5 to 500 µm.

In general, in accordance with the present invention, there is further provided an absorbent combination comprising a particulate absorbent as defined herein with a carrier.

DETAILED DESCRIPTION

The first object of the present invention is a particulate absorbent, for the absorption of liquids, comprising polysaccharide particles. The polysaccharide particles may comprise particles of glass-like polysaccharides, particles of glass-like polysaccharides occluding, in their internal structure, at least one surfactant or mixtures thereof, said particles:

having a size of up to 620 µm;

being at least 70% by weight of a glass-like type structure; and being:
  30 to 45% by weight of a size comprised between 620 and 420 µm;
  35 to 55% by weight of a size comprised between 420 and 210 µm; and
  5 to 25% by weight of a size up to 210 µm.

In accordance to the present invention, the polysaccharide may preferably be based on an amylaceous polysaccharide such as an amylose or an amylopectine or on a mixture of amylose and amylopectine.

A suited starting polysaccharide is a native unmodified polysaccharide, preferably a native unmodified starch, more preferably a grade A starch.

The grade A starch is preferably a wheat starch but may also be a corn, barley, potato, rye, manioc or milo or any other starch sources.

Essential features of grade A wheat starch are represented in following Table I.

TABLE I

Comparative features of Grade A starch obtained by the modified Martin and hydrocyclones processes.

| Features | Modified Martin Process | Hydrocyclones Process |
| --- | --- | --- |
| Humidity (%) | 10.50 | 11.4 |
| Ashes (% dry basis) | 0.31 | 0.22 |
| Total lipids (% dry basis) | 0.41 | 0.94 |
| Solubles (% dry basis) | 0.34 | 0.1 |

TABLE I-continued

Comparative features of Grade A starch obtained by the modified Martin and hydrocyclones processes.

| Features | Modified Martin Process | Hydrocyclones Process |
|---|---|---|
| Proteins (% dry basis) | 0.22 | 0.27 |
| PH | 5.90 | 6.5 |
| Residual (% dry basis) | 0.20 | 0.09 |
| Cediment (% dry basis) | 4.70 | 8 |
| Amylography and viscosimetry | | |
| Gelatinisation temperature (° C.) | 88.3 | 86.0 |
| Viscosity at 95° C. (UB) | 320 | 370 |
| Temperature peak (° C.) | 95 | 95 |
| Viscosity peak (° C.) | 340 | 385 |
| Viscosity at 95° C. and after 15 mins (UB) | 280 | 340 |
| Viscosity at 50° C. (UB) | 720 | 730 |
| Glue test | | |
| Viscosity (s) | 53 | 47 |
| Gel point (° C.) | 65.5 | 64.5 |
| Mousse test | | |
| After 15 mins (%) | 5.1 | 0 |
| After 30 mins (%) | 2.0 | 0 |

*Brabender units

From: Les Minoteries Ogilvie Ltd., Montreal, Canada

This starch is mainly constituted by granulates with a lentil form and with a size ranging from 25 to 40 μm.

Suited starting grade A wheat starches are those commonly used in paper, food, textile and fermentation industries. Moreover grade A wheat starches in their native as well in their glass-like form are commonly used as ingredient in food industry.

In accordance with the present invention, the particles of the glass-like polysaccharide and the particles of the glass-like polysaccharide occluding, in their internal structure, at least one surfactant, may have a size ranging from 5 to 500 μm (e.g. a size of about 300) μm.

The mean of the polysaccharide particles present in the particulate absorbent according to the invention may preferably ranges from 150 to 500 Φm and may more preferably be about 300 μm.

The method used for determining the size of said polysaccharides present in the particulate absorbent also name sieving method is defined as following:

- each of six sieves of, according to U.S. Standard, 30 mesh, 40 mesh, 50 mesh, 60 mesh, 100 mesh and 170 mesh are tarred,
- 100 grams of the sample is laid down on the first (30 mesh) sieve,
- the fraction of the sample which is not retained by the first sieve falls into the second (40 mesh),
- such a the selection process is repeated for each sieve,
- each sieve is mechanically waved for 20 minutes and then tarred again,
- then the rate of particles retained on each sieve is calculated for 100 grams of the initial sample.

The standard deviation was calculated from 10 batches corresponding to the production of 218 lots over 3 years.

The 10 standard deviation were calculated with the formula:

$$S = \frac{\sum f(x-\bar{x})^2}{n-1}$$

Wherein f is the frequency of the result (for example 16% of particles have a size comprised between 250 and 420 microns), x is the central value of the class (comprised between 250 and 420 microns preferably about 350 microns), $\bar{x}$ is the mean distribution of the lot and n is the number of results (100%).

The standard deviation is the average of these 10 standard deviations and the given range is the range between the lower standard deviation and the highest standard deviation.

The standard deviation of the particles of polysaccharides preferably ranges from 100 to 120 microns. According to a most preferred embodiment of the invention the standard deviation is about 110 microns.

The surfactant which is occluded in the internal structure of the glass-like polysaccharide is preferably an ionic surfactant comprising a linear alkyl moiety i.e. an ionic surfactant with a long alkyl linear chain. Mixtures of various surfactants are also suited in the meaning of the invention. As examples of suitable anionic surfactant with a long linear chain are alkyl carboxylates, cationic alkyls ammonium, alkyl sulfonates and alkyl phosphates with at least 11 carbon atoms. Preferably the long linear chain (i.e. the linear alkyl moiety comprises or) has from 12 to 20 carbon atoms. More particularly adapted in the meaning of the invention is a surfactant selected in the group constituted by fatty acid salts such as sodium stearate.

The moisture content of the glass-like polysaccharide is up to 13%.

The selected particles of glass-like polysaccharides of the invention are obtained by screening of the particles of a glass-like polysaccharide.

Said glass-like polysaccharides may be partially crystallized. They have, at least 70%, more preferably at least 80%, and according to the best mode 100% of a glass-like type structure.

The latter glass-like polysaccharides (for example, glass-like starch) absorbent are further characterized by their elementary composition, which elementary composition comprises:

from 33 to 40 weight percent of carbon;
from 53 to 59 weight percent of oxygen;
from 6.6 to 7.5 weight percent of hydrogen;
less than 0.15 weight percent of sulphur;
less than 0.6 weight percent of chloride; and
residuals,
the weight percent being expressed by total weight of said glass-like polysaccharide (for example, glass-like starch).

Residuals means nitrogen, sodium, calcium and phosphor ions or any other unidentified compounds, unidentified materials or mixture thereof.

The glass-like polysaccharides (for example, glass-like starches) according to the invention, as determined by Infrared Spectroscopy conducted by using KBr as reference, comprises hydroxy functions, as well as relative humidity occluded inside the glass-like polysaccharides.

A preferred family of glass-like polysaccharide (for example, glass-like starch) according to the invention is constituted by those glass-like polysaccharide (for example, glass-like starch) absorbent having the 3 (three) following intensive infrared bands respectively at:

$1649 \pm 5$ cm$^{-1}$;
$3446 \pm 5$ cm$^{-1}$; and
$3504 \pm 5$ cm$^{-1}$, which bands characterize the presence of water in the polymeric structure.

BRIEF DESCRIPTION OF THE FIGURES

FIG. 4 is a granulometric profile for a gelatinized starch;

FIG. 5 is a cross-sectional schematic illustration of an example of an absorbent structure in accordance with the present invention.

Figure 1:
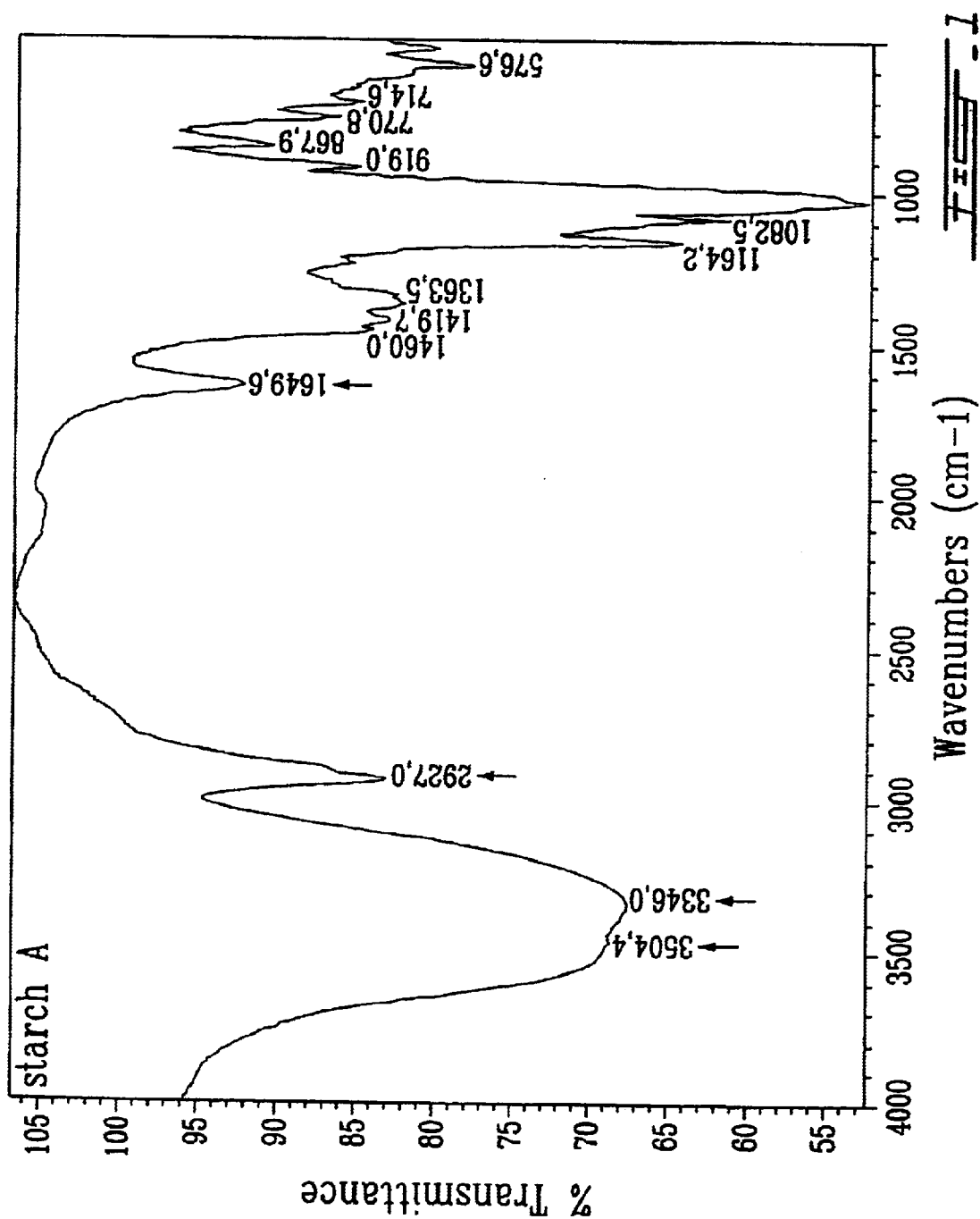
FIG. 1 is an IR diagram for a glass-like starch produced from a wheat grade A starch.

The particulate absorbents according to the invention exhibit a strong absorbency for polar liquids and for physiological fluids, particularly a strong absorbency by aqueous fluids, and more particularly a stronger absorbency for fluids selected in the group constituted by water, mixtures of water and of at least one in water soluble solvent such as an alcohol or a ketone, urine and blood serum.

The particulate absorbents according to the invention are particularly efficient for polar liquids and for physiological aqueous fluids with a pH ranging from 2 to 11.

When the pH of the aqueous solution is less than 2, the polymeric structure which constitutes the particles of the particulate absorbent is hydrolysed.

The water retention's properties were checked for different pH ranging from 2 to 11, according to the Protocol of Retention according to method 8. No change was noted for the retention properties over a period of 15 minutes. Stability tests by pH of 2 or 11 may be qualified as extreme tests for the considered applications.

Suitable aqueous solutions are aqueous solutions with ethanol and/or with acetone.

Those glass-like polysaccharides according to the invention which do not include a surfactant in their internal structure may be prepared by gelatinization, which generally consists in heating an aqueous mixture of native starch granules to a temperature at which the granules breakdown and the individual starch molecule disperse into solution. Then the thereby obtained gelatinized starch is dried and ground. Such gelatinization proceedings are described inter alia in U.S. Pat. No. 5,360,903 and in U.S. Pat. No. 3,706,598, the entire content of the documents are incorporated by reference.

Those particulate absorbent for fluids according to the first object of the invention wherein glass-like polysaccharides occlude a material with tensio-active properties in their internal polymeric structure may be prepared by the following process which constitutes the second object of the present invention.

More generally, this process which applies to the preparation of particles of glass-like polysaccharides occluding, in their internal structure, at least one surfactant, said particles:

having a size up to 620 μm; and
being at least 70% of a glass-like type structure; and
comprises the steps of:
heating a polysaccharide in the presence of water for 0.5 to 2.5 hours at a temperature ranging from 70 to 97° C. so as to obtain a warm gelatinized polysaccharide,
drying the warm gelatinized polysaccharide obtained in step (1) so as to obtain a glass-like polysaccharide; and
grinding the dry glass-like polysaccharide obtained in step (2) to particles and recovering preferably by screening the particles to a size of up to 620 μm,
wherein:
at least one surfactant is added in step (1);
the weight % of polysaccharide in water ranges from 3.2 to 50; preferably from 4.8 to 16.5% and more preferably about 9.1%; and
the weight % of surfactant in the polysaccharide ranges from 6 to 10, being preferably of about 8.

In step (1), the polysaccharide may be heated in the presence of water preferable for 2 hours at a temperature which preferably ranges from 75 to 95° C.

In step (2), the gelatinized polysaccharide is preferably dried in a convection furnace, at a temperature preferably comprised between 40 to 50° C.

In step (3), the glass-like polysaccharide obtained in step (2) is ground with a grinder of any type.

A third object of the present invention is an absorbent composition comprising:

77 to 83% by weight of a particulate absorbent for liquid as defined in the above mentioned first object of the invention;
15 to 17% by weight of an insoluble carboxymethylcellulose;
2 to 6% by weight of a high viscosity carboxymethylcellulose.

In the meaning of the invention "insoluble" means carboxymethylcelluloses without any solubility or with a low solubility under specific conditions and therefore with a very high viscosity.

Suitable insoluble carboxymethylcelluloses may have, according to ASTM D-1439, a D.S. ranging from 0.65 to 0.9 and preferably about 0.78 and have a viscosity ranging from 7000 to 12000 and preferably of about 7500 mPas (by a 1% water solution, at 30 rpm, with a spindle no.4).

Suitable high viscosity carboxymethylcelluloses may have, according to ASTM D-1439, a D.S. ranging from 0.8 to 0.95 and preferably about 0.9 and have a viscosity of ranging from 1500 to 2500 and preferably about 2000 mPas (by a 1% water solution at 25° C., according Brookfield LVF spindle no.3 at 30 rpm).

Such compositions are biodegradable, non-hygroscopic, hypoallergenic and stable on a wide pH range.

A fourth object of the invention is an absorbent composition comprising:
- 79 to 92% by weight of a particulate absorbent for liquid as defined in the above-mentioned first object of the invention;
- 4 to 10.5% by weight of a xanthane gum; and
- 4 to 10.5% by weight of a guar gum.

Under such specific concentration a synergistic effect is reached for the absorption.

According to a more preferred embodiment of the invention, the xanthane gum has a viscosity, ranging from 1400 to 1650 cps at a concentration of 1% in water with 1% of KCI and a viscosity ranging from 130 to 180 cps, at 0.2% in water with 1% of KCI, the viscosity being measured by preparing a 1% salt solution of a product by slowly adding a dry blend of 3.0 g product and 3.0 grams potassium chloride to 250 ml of distilled water in a 400 ml beaker, while stirring at 800 rpm using a low-pitched propeller type stirrer, by adding an additional 44 ml of distilled water, rinsing the walls of the beaker and continue stirring at 800 rpm for two hours and, at the end of the period, by adjusting the temperature of the solution to 25° C., by vigorously stirring by hand in a vertical motion to eliminate any thixotropic effects or layering, and immediately measuring the viscosity by using a LV model of the Brookfield viscometer at 60 rpm with No. 3 spindle, and the guar gum has a viscosity after 24 hours of at least 3500 cps, after 30 minutes of 2800 cps.

Guar gums which are usually extracted from the albumen of certain seeds consists of mannose units attached together by $\alpha(1-4)$ bounds. These units form a main chain on which galactose units are attached. The latter units are attached to mannose by bounds of the $\beta(1-6)$ type. There is one galactose for two mannose. Guar gums are used for the ability to improve hydration in cold water to viscous solutions.

Xanthane gums which are commonly produced during the aerobic fermentation of sugar by the yeast *Xanthomonas campestris* have a main D-glucose chain bounded in $\beta(1-4)$ by the bounding of one glucuronic acid with mannose units. The DS is of 0.33.

Particularly adapted guar and xanthane gums are those commonly used in food industry.

Such compositions are biodegradable and present a good non-hygroscopic and hypoallergenic potential.

A fifth object of the present invention is an absorbent combination comprising a particulate absorbent for liquid as defined in the above-mentioned first object and/or of an absorbing composition as defined in the above-mentioned third and fourth object, with a carrier.

The carrier may be an air laid, chemically bonded tissues, chemically bonded non-woven wet laid, hydro-entangled fabrics, meltblows or laminated structures.

The air laid carrier is preferably an air laid latex, an air laid thermal bonded or a dry laid (carded).

A sixth object of the present invention is constituted by:
- breast pads (nursing pads),
- food pads,
- diapers (disposable and non disposable infant diapers, training pants),
- adult incontinence products (personal pads, bed pads, briefs),
- feminine hygiene products (tampons, sanitary napkins), and
- surgery and surgical pads or bandages, in which a particulate absorbent according to the first object and/or an absorbing composition according to the third and/or to the fourth object of the present invention has been incorporated.

According to a preferred embodiment of the invention the preferred absorbent combination is selected in the group constituted by diapers (such as sanitary napkin, baby-diaper, adult incontinence products, alimentary blotting paper, medical blotting paper). Particularly preferred is a biodegradable diaper.

Example of a diaper according to the invention comprises:
- a first external layer permeable to physiological fluids;
- a central matrix essentially made of an absorbing material; and
- a second external layer impermeable to physiological fluids and to aggregates formed by said physiological fluids with the absorbing material present in the central matrix which is entrapped between both external layers, characterized in that the absorbing material in the central matrix consists of 2 to 27%, preferably of 3 to 17% (in weight by total weight of the absorbing material present in the matrix) of at least one particulate absorbent for liquid and/or of at least one absorbent composition according to the invention, the remaining part of the absorbing material in said central matrix being selected in the group constituted by natural fibres, semi-synthetic fibres, synthetic fibres, wood pulp, cellulose fibres, cotton, peat-moss and mixture thereof.

An example of an absorbent pad in which the particulate absorbent and/or the absorbing composition of the invention may be incorporated is U.S. Pat. No. 6,015,608 which is incorporated herewith by reference.

EXAMPLES

Preliminary References

The following methods have been used to evaluate the performances of the test samples:

Granulometry of the absorbent was measured according to the ASTM D2862-92 method modified with sieves of 600 μm, 425 μm, 300 μm, 150 μm, 90 μm and with a size lower than 90 μm.

The water solubility rate was measured according to the FSC 7930 method.

Speed of the water absorption was measured according the CAN/CGS-183, 2–94, article 9.1.2 modified method, absorption tomes of 30 s, 1 min, 2 min, 5 min, 15 min, 30 min and 720 minutes were used.

The volumetric mass was measured with a method consisting in measuring the apparent determined volume of an absorbent in a graduate cylinder made of glass.

The change of the volume of the absorbents in presence of water was measured according to the ASTM F716 article 11.2.1 modified method, instead of using 2 ml of solid absorbent for the tests, 1 gram of absorbent was used for the Lysorb® and between 0.1 and 0.2 grams for the other absorbents.

The amount of water in the absorbents (loss of weight) has been measured by drying samples at 105° C. for 24 hours.

Evaluation of the capacity of water diffusion in the absorbent was measured according to the ASTM F716 article 11.4 modified method, a 50 ml burette made of glass was used instead of specified tubes made of glass used in the method and the maximal deepness of the penetration of the liquid in the absorbent was noted.

Water Retention Capacity

From 100 to 200 mg of absorbent are weighed in a pre-weighed tube for centrifugation of 15 ml. 10 ml of water are added and immediately agitated with a stick for one minute.

The mixture stays for 15 minutes and then centrifugated for 5 minutes at 2000 rpm. The supernatant is discarded and the dottle constituted of the absorbent and the water retained in the form of a paste (similar to a gel) is weighed. The ratio=gram of retained water by gram of absorbent is determined.

Absorbtion Under Load The absorbency again pressure was measured according to the EDANA 442.1.99.

Free Swell Capacity was measured according to EDANA440.1-99.

Examples 1

A glass-like starch was produced from a wheat grade A starch, having the IR diagram represented in attached FIG. 1, by using the extrusion step described in example 4 of U.S. Pat. No. 5,360,903 except that no chemical agent was used. The resulting product was non-expanded, fully gelatinized and had a light brown-yellow colouration and is in form of pellets.

The pellets were ground to form particles after having been allowed to cool and cure for 24 hours. The cooled and cured pallets were then processed in a Raymond Laboratory Hammer Mill and screened on a 30 mesh U.S. standard sieve. The fraction retained on the sieve was recycled into the grinder. The pellets were fed into the mill at about 20 pounds per hour.

The resulting mixture of particles thereby obtained has the following composition:

| % retained | on Mesh US Standard |
| --- | --- |
| 0.5 | 30 |
| 40 | 40 |
| 32 | 60 |
| 12 | 70 |
| 10 | 100 |
| 4 | 170 |
| 1.5 | 170 and more |

Figure 2:
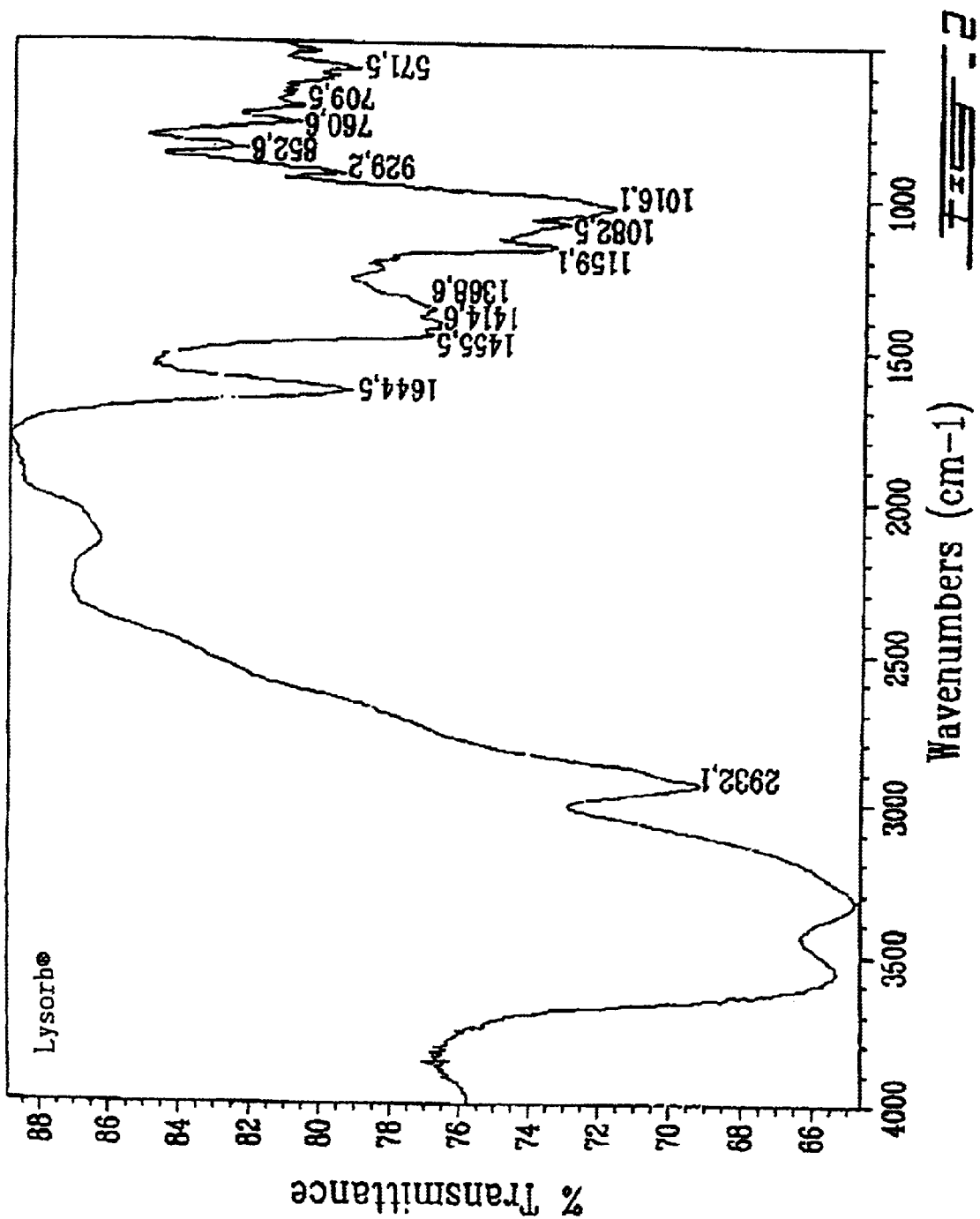
FIG. 2 is an IR diagram for a mixture of particles of a glass-like starch.

This mixture is further characterized by the IR diagram reported in attached FIG. 2 and called hereafter Lysorb®.

Examples 2—glass-like starch occluding a surfactant in its internal structure.

First part—occlusion of sodium alkyl sulfonate.

The grade A starch used in example 1 for preparing the glass-like starch in a mixture with 10 parts of water, wherein 9% (calculated on the weight basis of the starch) of sodium alkyl sulfonate for 1 part of grade A starch is added, is gelatinized at a temperature of 95° C. for 90 minutes.

At the end of the gelatinization, the mixture stays at room temperature until its temperature reaches about 25° C. then the mixture is dried.

At this stage, before drying, the gel exhibits the following viscosity features (measured with a Brookfield apparatus equipped with a number 4 Spindle) which are summarized in the following Table II:

TABLE II

| RPM | Shearing (1/sec) | Viscosity (Pa.sec) |
| --- | --- | --- |
| 0.3 | 0.065 | 112.721 |
| 0.6 | 0.129 | 112.725 |
| 1.5 | 0.323 | 103.033 |
| 3 | 0.647 | 86.116 |
| 6 | 1.293 | 60.001 |
| 12 | 2.587 | 39.838 |
| 30 | 6.467 | 21.917 |

Figure 3:
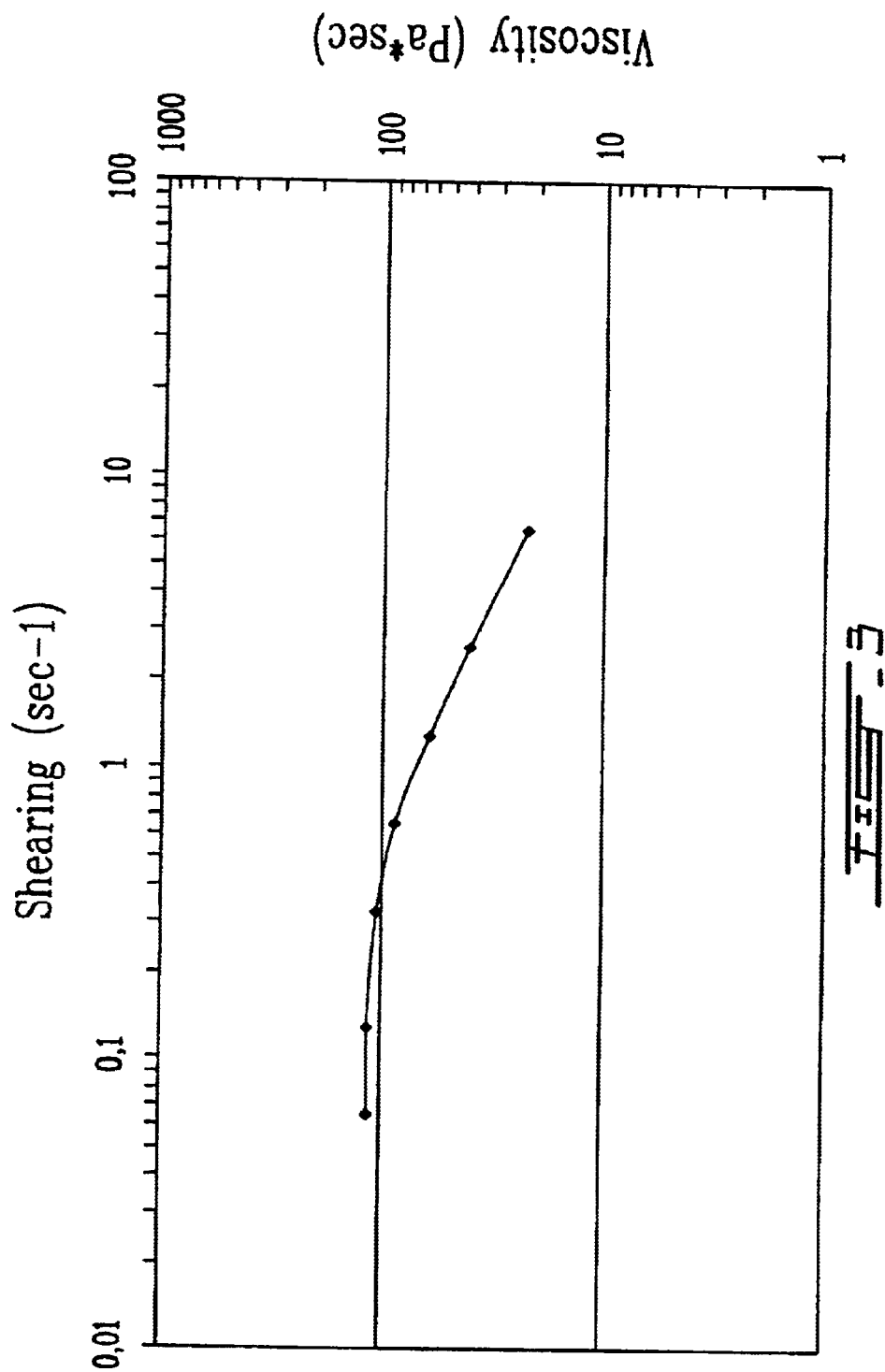
FIG. 3 is a viscosity profile for a gelatinized starch.

The viscosity profile is represented in the attached FIG. 3.

Such a behaviour is qualified as "shearthrinning" (with a Yield stress of 19.4 Pa). This means that a minimum stress of 19.4 Pa is necessary to fluidify the gel.

The drying of the "tray dried type" is then carried out at a temperature comprised between 40 and 50° C. for 24 hours so that the % of final humidity, according to the above mentioned method 6 reaches about 0%. After drying, a dry cake remains. The cake is ground to obtain absorbent particles.

Second Part—Occlusion of Sodium Stearate

A mixture of a starch as described in example 1 with 20 parts of water for one part of starch is added with 6% (calculated on the weight basis of starch) of sodium stearate.

The latter mixture is heated at a temperature of 95° C. for 20 minutes and the gelatinized starch thereby obtained is cooled, before drying, at ambient temperature until a temperature of about 25° C. is reached.

At this stage, the gel has a Yield stress of 15 Pa which is characterizing of shear thinning behaviour type. The viscosity of the gel measured according to the Brookfield LV model is about 24.7 Pa.sec at 1 s$^{-1}$.

A drying (of the tray dried type) is then carried out at a temperature comprised between 40 and 50° C. for 24 hours in order to obtain a final humidity rate measured according to the above defined method 6 which is of about 0%.

After drying, a cake remains.

The cake is ground in absorbent granules with a particle size ranging from 0 to 620 $\mu$m and with the particle profile described in Table III.

Comparative Example 3

A study of glass-like starch described in example 1 shows that its properties are dependant upon the selected granulometry. The fine particles exhibit an intense and rapid absorption but are less efficient during swelling under pressure. The fine particles are also sensible to saline ions. Coarser particles exhibit a better resistance to the pressure and are less sensible to saline ions. However the absorption is slower and less important.

The granulometric profile is represented on attached FIG. 4 and the corresponding measures summarized in the following Table III:

TABLE III

| % NaCl | Absorption | | | Retention | | | AAP |
| --- | --- | --- | --- | --- | --- | --- | --- |
|  | 0 | 0.2 | 0.9 | 0 | 0.2 | 0.9 | 0 |
| Mean 210 microns | 8.2 | 8.8 | 6.1 | 9 | 8.7 | 7.5 | 2.9 |
| Mean 290 microns | 7.9 | 8.8 | 7.5 | 8.4 | 8.4 | 8 | 4.5 |

The absorbency against pressure (AAP) was measured according to the EDANA 442.1-99 method. EDANA means European Disposables and Nonwoven Associations.

The retention was measured according to the above-defined method 8.

The absorption was measured according to the EDANA method 440.1-99.

Comparative Example 4

The absorption properties of:
the glass-like grade A starch obtained in part 1 of example 2 which occludes sodium alkyl sulfonate (SAS),
the glass-like starch obtained in part 2 of example 2 which occludes sodium stearate (SS); and
the glass-like grade A starch obtained by treating the grade A starch described in example 1 according to the gelatinisation process described in example 2 except that no surfactant was added during the gelatinisation, were compared.

The method used for the evaluation of the retention capacity is the above-defined method 8 of the preliminary references. The corresponding results are reported in the following Table IV:

TABLE IV

| Absorbent: glass-like polysaccharides | R(g/g) value in distilled water |
|---|---|
| SAS derivative | 21.3 |
| Stearate derivative | 60 |
| Grade A starch | 4.6 |

A significant improvement of the absorbency appears for the SAS and SS derivatives when compared to the grade A glass-like starch wherein no surfactant is occluded.

Example 5

Mixtures of the glass-like starch prepared in example 1 with a 100% xanthane gum commercialized under the code 91 and of guar gum commercialized under the code A-200. Both gums are commercialized by the Company Harold T Griffin were evaluated for their retention. The results of this evaluation are reported in the following table V:

TABLE V

| | Retention of Ternary Mixtures | | | | |
|---|---|---|---|---|---|
| Test Number | Guar % | XanthaneHT % | Lysorb ® % | Total % | Rentention ($H_2O$) |
| T1 | 0 | 10 | 90 | 100 | 14 |
| T2 | 0 | 20 | 80 | 100 | 26 |
| T3 | 10 | 0 | 90 | 100 | 12 |
| T4 | 20 | 0 | 80 | 100 | 15 |
| T12 | 5 | 15 | 80 | 100 | 27.5 |
| T13 | 3 | 10 | 87 | 100 | 16 |
| T14 | 4 | 9 | 87 | 100 | 16 |
| T17 | 5 | 5 | 90 | 100 | 15 |
| T18 | 6 | 6 | 88 | 100 | 20.6 |
| T19 | 7 | 7 | 86 | 100 | 25 |
| T0 | 0 | 0 | 100 | 100 | 7.8 |

The results show a synergetic effect obtained for the tertiary mixture when compared to the sum of the retention power of each component of the mixture.

The mixture T18 shows a retention of 20.6 and the mixture T19 shows a retention of 25 when a retention of 7.8 is reached for the glass-like starch of example 1.

Properties

Lyspill® compositions according to the invention, comprising particles of a glass-like grade A starch, an insoluble carboxymethylcellulose and a high viscosity carboxymethylcellulose were tested for their toxicity over microorganisms and for their biodegradability, by using the 310E method of the "Organization for Economic Co-operation and Development (OECD)".

The experimental conditions for degradation are summarized in following table VI:

TABLE VI

| Substance of Reference | Sodium Benzoate |
|---|---|
| Theorical starting concentration of the reference substance | 20 mg/l |
| Tested product | Lyspill ® |
| Inoculum | Actived mud, Valcartier |
| Inoculum concentration | 0.5 ml/l |
| Incubation temperature | 20 EC |
| Agitation | 175 rpm |
| Carbon analyser | Technicon |

Toxicity tests (not included in the OECD tests) which are a preliminary to the biodegradability tests reveal that the tested compositions do not inhibit the microorganism of a sample of an activated mud.

The corresponding biodegradability tests reveal a biodegradability of at least 46% after 2 weeks.

The particulate absorbent as well as the specific mixtures with carboxymethylcellulose (CMCs) and/or with xanthane and guar gums according to the invention are biodegradable and therefore, even when incorporated in disposable structures are not dangerous for the environment. This constitutes a determinant advantage over polyacryamides and other chemical superabsorbents generally used in disposable absorbent structures which are not biodegradable and which accumulates in the environment.

The particulate absorbent as well as the specific mixtures with CMC and/or with xanthane and guar gums according to the invention which do not irritate nor generate allergy in more than 2% of cases (in fact 100% in the present case) can be classified as hypoallergen as established by the result of a Consumer Product Testing.

When few persons had a negative response to the chemical absorbent usually present into absorbent personal care products.

Allergen Test According to Consumer Producing Testing

The objective of the test is to determine by repetitive epidermal contact the potential of a test material to induce primary or cumulative irritation and/or allergic contact sensitization or cumulative irritation and/or allergic contact sensitization.

Sixty (60) qualified subjects, male and female, ranging from 17 to 79 years were selected for the evaluation. Fifty-eight (58) subjects completed this study. The remaining subjects discontinued their participation for various reasons, none of which were related to the application of the test material.

The inclusion criteria were:

Male and female subjects, age 16 and over

Absence of any visible skin disease which might be confused with a skin reaction from the test material, Prohibition of the use of topical or systemic steroids and/or antihistamines for at least seven days prior to study initiation, Completion of a Medical History form and the understanding and signing of an Informed Consent form, Considered reliable and capable of following directions The exclusion criteria were:

Ill health,

Under a doctor's care or taking medication(s) which could influence the outcome of the study, Females must not be pregnant or nursing, A history of adverse reactions to cosmetics or other personal care products.

The material tested was the glass-like starch Lysorb® alone described in example 1.

The following methodology was used for the testing of Lysorb®:

The upper back between the scapulae served as the treatment area. Approximately 0.2 g of the test material, or an amount sufficient to cover the contact surface, was applied to the 1"×1" absorbent pad portion of a clear adhesive dressing manufactured by TruMed Technologies, Inc, Burnsville, Minn.

This pad was moistened with several drops of distilled water to ensure adherence of the test material. This was then applied to the appropriate treatment site to form a semi-occluded patch.

Introduction Phase

Patches were applied (3) times per week (e.g., Monday, Wednesday, and Friday) for a total of nine (9) applications. The site was marked to ensure the continuity of patch application. Following supervised removal and scoring of the first Induction patch, participants were instructed to remove all subsequent Induction patches at home, twenty-four hours after application.

The evaluation of this site was made again just prior to re-application. If a participant was unable to report for an assigned test day, one (1) makeup day was permitted. This day was added to the Induction period.

With the exception of the first supervised Induction Patch reading, if any test site exhibited a moderate (2-level) reaction during the Introduction Phase, application was moved to an adjacent area. Applications are discontinued for the remainder of this test phase, if a moderate (2-level) reaction was observed on this new test site. Applications would also be discontinued if marked (3-level) or severe (4-level) reactivity was noted.

Rest periods consisted of twenty-four hours following each Tuesday and Thursday removal, and forty-eight hours following each Saturday removal.

Challenge Phase

Approximately two (2) weeks after the final Introduction patch application, a Challenge patch was applied to a virgin test site adjacent to the original Induction patch site, following the same procedure described for Induction. The patch was removed and the site scored at the clinic twenty-four and seventy-two hours post-application.

Evaluation Key

=no visible skin reaction,

+=barely perceptible or spotty erythema;

1=mild erythema covering most of the test site;

2=moderate erythema, possible presence of mild edema;

3=marked erythema, possible edema;

4=severe erythema, possible edema, vesiculation, bullae and/or ulceration.

Results

In all the cases where the study was completely performed no visible skin reaction was detected. Therefore under the condition of the study, the test material, Lysorb®, did not indicate a potential for dermal irritation or for allergic contact sensitization.

Compostable Diapers

The particulate absorbents according to the invention which comprises particles selected from the group consisting of glass-like polysaccharides and of glass-like polysaccharides occluding at least a surfactant in their internal structure, as well as the specific combinations of the latter absorbents with specific celluloses or gums are particularly suitable as absorbing component of compostable diapers as those disclosed in U.S. Pat. No. 5,026,363 or in U.S. Pat. No. 5,743,895 both in the name of RMED International, Inc. Which documents are incorporated by reference to the present application.

U.S. Pat. No. 5,026,363 described more particularly a flushable diaper comprising, in combination, a three layered combined structure made of a thin, moisture permeable, biodegradable material, wherein the middle layer of said three layered combined structure is made of a thin, high moisture absorbing, breathable, biodegradable material.

The biodegradable particulate absorbents as well as the specific combination of the invention may advantageously be present in the middle layer of said flushable diaper for example in combination with wood pulp type material which is also a biodegrable constituting element of the middle layer.

Such a flushable diaper wherein the bottom will be classified as entirely or substantially biodegradable are particularly suited for ecology purposes.

U.S. Pat. No. 5,743,895 described a disposable diaper in which structure the absorbent of the invention can be advantageously incorporated as further biodegradable component.

The particulate absorbents of the invention are obtained from a renewable natural source are biodegradable, non-hygroscopic, hypoallergen and exhibiting a nearly ideal acquisition profile adaptable to the considered application.

Moreover, the particulate absorbent as well as specific mixtures with CMC and/or with xanthane and guar gums does not abrase the matrix in which they are incorporated for their absorbing properties. Therefore the corresponding diaper would not degrade by handling or transportation. Neither will mechanical degradation of the diaper, generated by the granules of absorbent, will occur during manufacturing.

When the absorbents usually incorporated in the industry of absorbent structures are responsible for perforations (usually called pin holes) frequently but not exclusively observed in the sheet (back sheet) in ultra-thin structures.

Summary

The particulate absorbent and the absorbing compositions according to the invention are classified as hypoallergen, as biodegradable, as non-hygroscopic and as stable on a wide pH range according to following definitions:

hypoallergen means that according to the protocol #1.01 of the above defined Consumer Product testing, when applied to 50 person:

nobody presents an irritation grade of 4;

nobody presents an irritation grade of 3;

nobody presents an irritation grade of 2;

a maximum of one tested person presents the irritation grade 1; and a maximum of 2 persons present the irritation grade +; and at all, a maximum of 2 persons present an irritation grade other than 0, wherein:

=no visible skin reaction,

+=barely perceptible or spotty erythema;

1 =mild erythema covering most of the test site;

2=moderate erythema, possible presence of mild edema;

3=marked erythema, possible edema;

4=severe erythema, possible edema, vesiculation, bullae and/or ulceration (according to these definition the Lysorb® product is hypoallergen), biodegradable means that according to the OECD 301-E method at least 50% of the tested particulate absorbent or of the tested absorbing composition is degraded (the 215 product which has been tested according to the method is degraded for 46% in 14 days can therefore be classified as biodegradable, the same applies to the glass-like polysaccharide Lysorb®), non-hygroscopic means that no retention of humidity occurs after 60 minutes, as measured according to the following exemplified test conducted with Lysorb®; the water retention of the absorbent was evaluated by placing a cup containing 1 gram of the absorbent and a cup containing 20 ml of water in a closed test room for 5 hours, the humidity gap immediately at the exit of the test room is relatively low, at about 6 weight %, this humidity is not strongly retained since a complete release in the environment occurs after 60 minutes at ambient, and stable over a wide pH range for an absorbent according to the invention, means a 100% stability of the retention's capacity when tested, according to the method 8, for different pH ranging from 2 to 11, for 15 minutes (such a stability tests by pH as low as 2 and by a pH as high as 11 may be qualified as extreme tests).

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

FIG. 5 illustrates in schematic cross-section an example of an absorbent structure which may incorporate in the central part thereof a particle absorbent as described herein:

In FIG. 5 the various elements have the following reference numbers:

represents a first external layer permeable to liquids.

represents an air layer which may as desired be dispense with.

represents a central matrix made of an absorbing material.

represents an air layer which may as desired be dispense with.

represents a second external layer impermeable to liquid.

The liquid (0) goes through the first external layer (1), through the air layer (2), is captured by the absorbing material (6) inside of the matrix (3).

The external layer (5) represent a security layer for stopping any liquid which would not be captured by the absorbing material (6) in the matrix (3).

In relation to the absorbent structure, the particles may be held to the carrier in any known suitable manner keeping in mind the function of the absorbent.

The embodiments of the invention in which an exclusive property or privilege is claimed are defined as follows:

1. A method for the absorption of a liquid comprising contacting a liquid with a particulate absorbent, said particulate absorbent comprising particles of glass-like polysaccharides, said particles:

having a size up to 620 µm;

being at least 70% by weight of a glass-like type structure; and being:
  30 to 45% by weight of a size comprised between 420 and 620 µm;
  35 to 55% by weight of a size comprised between 210 and 420 µm; and
  5 to 25% by weight of a size up to 210 µm.

2. A method according to claim 1 wherein said glass-like polysaccharides are derived from starch by gelatinization.

3. A method according to claim 2 wherein said starch has a granulate size ranging from 25 to 40 µm.

4. A method according to claim 3 wherein said starch is a grade A wheat starch.

5. A method according to claim 4 wherein said glass-like starch comprises:

from 33 to 40 weight percent of carbon;

from 53 to 59 weight percent of oxygen;

from 6.6 to 7.5 weight percent of hydrogen;

less than 0.15 weight percent of sulfur;

less than 0.6 weight percent of chloride; and residuals, the weight percent being expressed by total weight of said glass-like starch.

6. A method according to claim 5 wherein said glass-like starch is characterized by 3 (three) intensive infrared bands respectively at:

$1649 \pm 5$ cm$^{-1}$;

$3446 \pm 5$ cm$^{-1}$; and $3504 \pm 5$ cm$^{-1}$.

7. A method according to claim 1 wherein the particles of the glass-like polysaccharide have a size ranging from 5 to 500 µm.

8. A method for the absorption of a liquid comprising contacting a liquid with a particulate absorbent, said particulate absorbent comprising particles of unmodified glass-like polysaccharides wherein said particles have a size of up to 620 µm.

9. A method according to claim 8 wherein said particles are at least 70% by weight of a glass-like type structure.

10. A method according to claim 8 wherein the particles have a size ranging from 5 to 500 µm.

11. A method for the absorption of a liquid comprising contacting a liquid with an absorbent combination, said absorbent combination comprising a particulate absorbent as defined in claim 8 with a carrier.

12. A method according to claim 2 wherein said particles of glass-like polysaccharides have a standard deviation comprised between 100 and 120 µm.

* * * * *